United States Patent [19]

Kellogg

[11] 4,376,076

[45] Mar. 8, 1983

[54] BIS-ESTERS OF 1,1-ALKANEDIOLS WITH 6-BETA-HYDROXYMETHYLPENICILLANIC ACID 1,1-DIOXIDE

[75] Inventor: Michael S. Kellogg, Waterford, Conn.

[73] Assignee: Pfizer Inc., New York, N.Y.

[21] Appl. No.: 380,174

[22] Filed: May 20, 1982

Related U.S. Application Data

[60] Division of Ser. No. 246,505, Mar. 23, 1981, Pat. No. 4,342,768, which is a continuation-in-part of Ser. No. 86,864, Oct. 22, 1979, Pat. No. 4,287,181.

[51] Int. Cl.³ .................. C07D 499/00; A61K 31/43
[52] U.S. Cl. ........................ 260/245.2 R; 424/270; 424/271
[58] Field of Search ............... 260/245.2 R; 424/270

[56] References Cited

U.S. PATENT DOCUMENTS 4,244,951  1/1981  Bigham .................. 424/250
4,309,347  1/1982  Bigham .................. 424/271

FOREIGN PATENT DOCUMENTS 2044255  11/1980  United Kingdom .

*Primary Examiner*—Nicholas S. Rizzo
*Attorney, Agent, or Firm*—Charles J. Knuth; Albert E. Frost; Robert K. Blackwood

[57] ABSTRACT

Bis-Esters of 1,1-alkanediols with 6-beta(hydroxymethyl)penicillanic acid 1,1-dioxide and 6-betaacylaminopenicillanic acids are useful as antibacterial agents. Intermediates useful for the preparation of these compounds include halomethyl, alkylsulfonyloxymethyl and arylsulfonyloxymethylesters of 6-beta(hydroxymethyl)penicillanic acid 1,1-dioxide and 6-beta-aminopenicillanoyloxymethyl-6'-beta-(hydroxymethyl)penicillanate 1,1-dioxide.

10 Claims, No Drawings

BIS-ESTERS OF 1,1-ALKANEDIOLS WITH 6-BETA-HYDROXYMETHYLPENICILLANIC ACID 1,1-DIOXIDE

CROSS REFERENCE TO RELATED APPLICATION

This application is a division of copending application Ser. No. 246,505, filed Mar. 23, 1981, now U.S. Pat. No. 4,342,768, which is a continuation-in-part of application Ser. No. 086,864 filed Oct. 22, 1979 now U.S. Pat. No. 4,287,181.

BACKGROUND OF THE INVENTION

One of the most well-known and widely used class of antibacterial agents are the so-called beta-lactam antibiotics. These compounds are characterized in that they have a nucleus consisting of a 2-azetidinone (beta-lactam) ring fused to a thiazolidone, a dihydro-1,3-thiazine or other similar ring system. When the nucleus contains a thiazolidone ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin, amoxicillin, hetacillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or caphalosporin, it can increase or enhance the antibacterial effectiveness of the penicillin or caphalosporin against certain beta-lactamase producing microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components against beta-lactamase producing microorganisms.

The present invention relates to a series of bis-1,1-alkanediol esters of 6-beta-(hydroxymethyl)penicillanic acid 1,1-dioxide and penicillins commonly used in clinical practice. These esters are readily hydrolyzed in vivo to yield the penicillin and 6-beta-(hydroxymethyl)penicillanic acid 1,1-dioxide, a particularly potent inhibitor of microbial beta-lactamases which enhances the effectiveness of the penicillin. The invention further relates to intermediates useful in the preparation of these 1,1-alkanediol esters.

Bis-esters of beta-lactam antibiotics and beta-lactamase inhibiting substances have been the subject of earlier reports, in particular the bis 1,1-alkanediol esters of beta-lactam antibiotics and penicillanic acid 1,1-dioxide (British Patent Application No. 2,044,255 and U.S. Pat. No. 4,244,951). However, the present compounds show a broader spectrum of activity than these earlier compounds, for example showing a high level of activity against beta-lactamase producing strains of *Pseudomonas aeruginosa* and *Enterobacter cloacal*, organisms against which the earlier compounds show little or no activity.

SUMMARY OF THE INVENTION

Particularly valuable antibacterial compounds of the present invention are of the formula

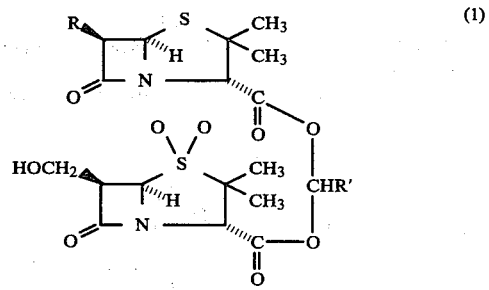

including the pharmaceutically-acceptable salts thereof, wherein R is 2-phenylacetamido, 2-phenoxyacetamido, D-2-amino-2-phenylacetamido, D-2-amino-2-(4-hydroxyphenyl)acetamido, 2-carboxy-2-phenylacetamido, 2-carboxy-2-(2-thienyl)acetamido, 2-carboxy-2-(3-thienyl)acetamido, D-2-(4-ethyl-2,3-dioxopiperazinocarbonylamino)-2-phenylacetamido or 2,2-dimethyl-4-phenyl-5-imidazolidinon-1-yl; and R' is hydrogen or methyl.

The expression "pharmaceutically-acceptable salts" is intended to encompass pharmaceutically-acceptable cation salts when the side chain R contains a carboxy group, and pharmaceutically-acceptable acid addition salts when the side chain R contains an amino group.

Of the compounds (1), those compounds wherein R' is hydrogen are preferred. Within this subgenus, the species most preferred are those wherein R is:
D-2-amino-2-phenylacetamido;
2-carboxy-2-phenylacetamido;
D-2-amino-2-(4-hydroxyphenyl)acetamido; and
2-phenylacetamido.

Particularly valuable intermediates of the present invention are compounds of the formula

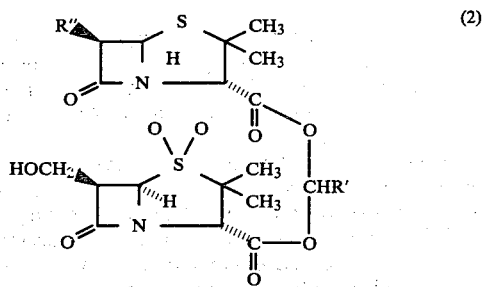

wherein R' is hydrogen or methyl and R" is amino or the D-form of

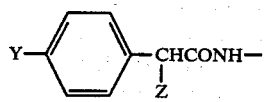

wherein Y is hydrogen or hydroxy and Z is azido, benzyloxycarbonylamino or 1-carbomethoxy-1-propen-2-ylamino.

Within this class of intermediates the preferred compounds have R' as hydrogen; within this subgenus the most preferred compounds are those wherein R" is:
amino;
D-2-azido-2-phenylacetamido; or
D-2-(benzyloxycarbonylamino)-2-(p-hydroxyphenyl)acetamido.

Other valuable intermediates are of the formula

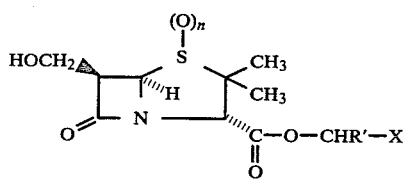

wherein n is zero or an integer of value 1 or 2; R' is hydrogen or methyl; and X is chloro, bromo, iodo, $(C_1-C_4)$alkylsulfonyloxy, benzenesulfonyloxy or toluenesulfonyloxy. In this series preferred compounds have R' as hydrogen. Within this subgenus the most preferred compounds have:
n as 0 and X as chloro;
n as 1 and X as chloro;
n as 2 and X as chloro; and
n as 2 and X as iodo.

Yet other valuable intermediates are of the formulae

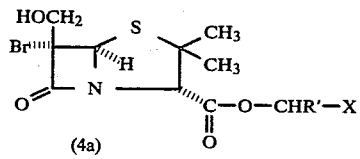

and

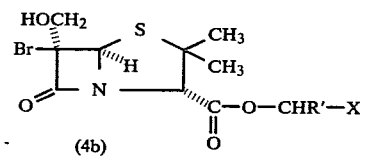

wherein R' is hydrogen or methyl and X is chloro, bromo, iodo, $(C_1-C_4)$alkylsulfonyloxy, benzenesulfonyloxy or toluenesulfonyloxy. The preferred compound in this series is of the formula (4a) and has R' as hydrogen and X as chloro.

Also encompassed by the present invention are pharmaceutical compositions of the antibacterial compounds of the formula (1) suitable for treating a bacterial infection in a mammalian subject. The present compounds can be dosed either parenterally or orally, but are particularly advantageous when given via the oral route.

Further encompassed by the present invention is a method for treating bacterial infections in a mammal which comprises administering to said mammal an antibacterially effective amount of an antibacterial compound of the formula (1). The preferred route of administration for said treatment is oral. The compounds are well absorbed and are hydrolyzed in vivo to the penicillin antibiotic and the beta-lactamase inhibitor, which then strongly potentiates the activity of the penicillin against a particularly broad spectrum of pathogenic organisms.

DETAILED DESCRIPTION OF THE INVENTION

This invention relates to derivatives of 6-beta-(hydroxymethyl)penicillanic acid 1,1-dioxide, which is represented by the following structural formula

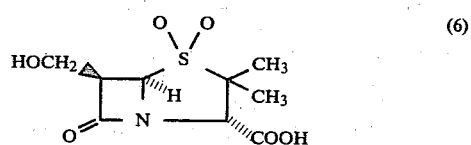

In formula (6), broken line attachment of a substituent to the bicyclic nucleus indicates that the substituent is below the plane of the bicyclic nucleus. Such a substituent is said to be in the alpha-configuration. Conversely, heavy line attachment of a substituent to the bicyclic nucleus indicates that the substituent is attached above the plane of the nucleus. This latter configuration is referred to as the beta-configuration.

Using this system, the compounds of formulae (1) and (2) are named as 6-beta-substituted derivatives of 1-(penicillanoxyloxy)alkyl 6'-beta-(hydroxymethyl)-penicillanate 1',1'-dioxide (7), in which the 1-position of the alkyl group and the 1-position of the first ring system is unambiguous under the nomenclature system, but in which primed and unprimed locants are used to distinguish between the two ring systems, viz:

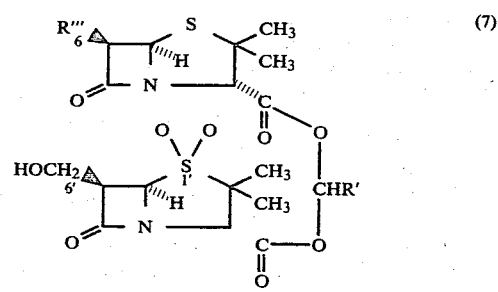

In one method of the present invention certain compounds of formulae (1) and (2) are prepared by reacting a carboxylate salt of the formula

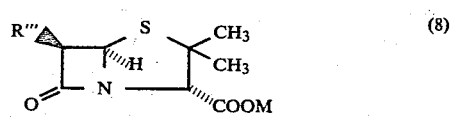

with a compound of the formula

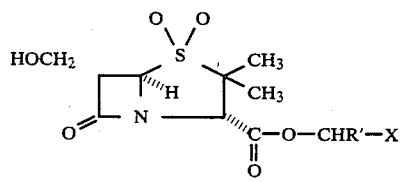

(9)

wherein R' and X are as previously defined; R'" is 2-phenylacetamido, 2-phenoxyacetamido, D-2-(4-ethyl-2,3-dioxopiperazinocarbonylamino-2-phenylacetamido, 2,2-dimethyl-4-phenyl-5-imidazolidinon-1-yl, 2-benzyloxycarbonyl-2-(2-thienyl)acetamido, benzyloxycarbonylamino, or

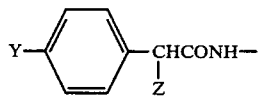

wherein Y and Z are as defined above; and M is a carboxylate salt forming cation. A variety of cations can be used to form the carboxylate salt in the compound of formula (8), but salts which are commonly used include: alkali metal salts, such as sodium and potassium salts; alkaline earth metal salts, such as calcium and barium salts; tertiary amine salts, such as trimethylamine, triethylamine, tributylamine, diisopropylethylamine, N-methylmorpholine, N-methylpiperidine, N-methylpyrrolidine, N,N'-dimethylpiperazine and 1,2,3,4-tetrahydroquinoline; and quaternary ammonium salts such as tetrabutylammonium salts. The quaternary ammonium salts are preferred salts, since the reaction between compounds of the formulae (8) and (9) is unusually rapid and degradation of the beta-lactams is thereby kept to an absolute minimum.

Said reaction between a compound of formula (8) and a compound of formula (9) is usually carried out by contacting the reagents in a polar, organic solvent, at a temperature in the range from about 0° to about 80° C., and preferably from 0° to 35° C. The compounds of formulae (8) and (9) are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. A low boiling solvent, readily removed by vacuum stripping is also preferred. Typical solvents which can be used include acetone, N,N-dimethylformamide, N,N-dimethylacetamide and N-methylpyrrolidone. The reaction time varies according to a number of factors, but at about 25° C. reaction times of a few minutes to several hours, e.g., 12 to 24 hours, are commonly used, depending particularly on the values of M and X. When M is quaternary ammonium (e.g., tetrabutylammonium) and X is iodo, advantageously short reaction times (e.g., 3-30 minutes) can generally be used. Reactions are conveniently monitored by standard silica gel thin layer chromatographic methods, specifically exemplified below. When X is chloro or bromo, it is sometimes advantageous to add up to about one molar equivalent of an alkali metal iodide, which has the effect of speeding up the reaction.

It will be evident from the above discussion that when the desired antibacterial compound (1) contains a carboxy group or an amino group, a protected or precursor form of the carboxy or amino group is employed. Conveniently these are such groups as a benzyl ester of the carboxy group (benzyloxycarbonyl), an azido group, or a benzyloxycarbonylamino (carbobenzoxyamino) group which are readily hydrogenolyzed, respectively, to carboxy, amino and amino. These hydrogenolyses are carried out by methods well-known in the art, viz., hydrogenation over an appropriate catalyst, such as palladium, platinum, or rhodium, optionally on a carrier such as carbon, calcium carbonate, or alumina, in an inert solvent, in such manner that degradation is minimized. Thus conditions are preferably near-neutral at ambient temperature or lower, and conveniently, at low to moderate pressure (e.g., 1 to 7 atmospheres). Higher pressures, e.g., up to 70 atmospheres, can be used but offer no advantage. By "inert solvent" is meant one which will finitely solubilize the starting material, without significantly reacting with starting material(s), product(s) or reagent(s) (in this case hydrogen and catalyst). The preferred solvents for the hydrogenolysis are also those which are volatile and in which product is also soluble, so that product can be recovered by simple evaporation in vacuo (or freeze drying, as appropriate) of the filtrate after recovery of catalyst. The preferred catalyst for the present hydrogenolysis is palladium on carbon. Optimal conditions (e.g., time, level of catalyst, batch of catalyst) for the hydrogenolysis of any given compound of the present invention are readily determined by monitoring with thin-layer chromatography, using methods as detailed in specific Examples.

The starting compounds of the formula (8) are well known in the penicillin art, either in the form of the free acids or in the form of various metal salts. The preferred salts; i.e., the quaternary ammonium salts, of the compounds of formula (8) are readily prepared by reaction of a molar equivalent of the corresponding quaternary ammonium hydroxide with the free acid form of (8) in a two phase, aqueous-organic system. The quaternary salt is isolated by simple evaporation of the organic layer; thus, a low boiling solvent such as methylene chloride is preferred.

The starting compounds of the formula (9) are conveniently prepared from 6,6-dibromopenicillanic acid according to methods detailed in the specific Examples below, employing intermediates of the formulae (3), (4a) and (4b) depicted above.

A variation of the foregoing method of preparing a compound of formula (7) involves reaction of a compound of the formula

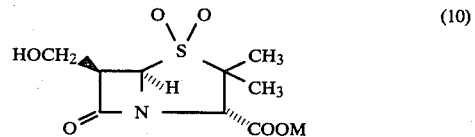

(10)

with a compound of the formula (11)

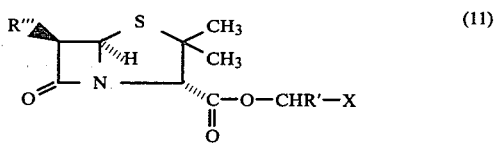

(11)

wherein R', R''', M and X are as defined previously, employing reaction conditions as defined above for the reverse reaction. In this case when X is chloro, bromo or iodo, the starting esters (11) are prepared by reaction of the corresponding metal salt with ICH$_2$X' wherein X' is chloro, bromo or iodo, and when X is (C$_{1-4}$)alkylsulfonyloxy, benzenesulfonyloxy or toluenesulfonyloxy, by reaction with the appropriate reactant CH$_2$(OSO$_2$R°)$_2$ wherein R° is methyl, p-tolyl, phenyl or n-butyl. Said reactants, if not known, are prepared as described by Emmons et al., J. Am. Chem. Soc. 75, 2257 (1953). The starting compound (10) is prepared by hydrogenolysis of benzyl 6-beta-(hydroxymethyl)penicillanate 1,1-dioxide which in turn is derived drom 6,6-dibromopenicillanate according to methods detailed in specific Examples 1-3 below.

In yet another method according to the present invention, compounds of the formula (7) are prepared by acylation of the compound of the formula

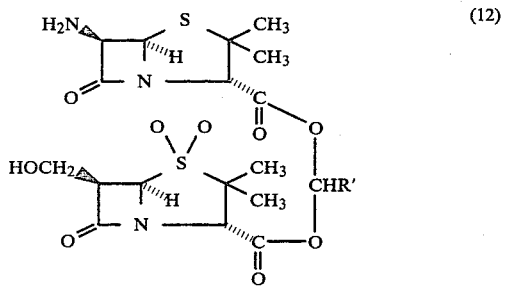

using a variety of methods well known in the penicillin art. For example, compound (12) is reacted with essentially one equivalent of an acid chloride such as phenylacetyl chloride, phenoxyacetyl chloride, or the mono acid chloride of phenylmalonic acid to yield, respectively and directly, compounds of the formula (1) wherein R is 2-phenylacetamido, 2-phenoxyacetamido or 2-carboxy-2-phenylacetamido. The reaction is conveniently carried out in an anhydrous organic solvent in the presence of a molar equivalent of a tert-amine such as triethylamine or N-methylmorpholine. Many solvents are suitable, but low boiling solvents such as methylene chloride or acetone are preferred. As a further Example, the amine (12) is coupled with the appropriate acid using standard mixed anhydride procedures or dehydrating agents such as carbodiimide, again using conditions, reagents and methodology well known in the penicillin art.

The hetacillin analogs, i.e., the compounds of the formula (1) wherein R is 2,2-dimethyl-4-phenyl-5-imidazolidinon-1-yl, are alternatively prepared by allowing the ampicillin analog, i.e., the compound of the formula (1) wherein R is D-2-amino-2-phenylacetamido, to stand in acetone at ambient temperature for 2-3 days.

The pharmaceutically-acceptable cationic salts of those compounds of the present invention having a free carboxylic acid group are readily prepared by standard methods. For example, an equivalent of the corresponding cationic hydroxide, carbonate or bicarbonate is combined with the carboxylic acid in an organic or aqueous solvent. The salt is isolated by concentration and/or the addition of a non-solvent. If desired, the salt can generally be isolated directly from a reaction mixture, without isolation of the free acid form. Pharmaceutically-acceptable cationic salts include, but are not limited to, those formed with sodium, potassium, calcium, N,N'-dibenzylethylenediamine, N-methylglucamine and diethanolamine.

The pharmaceutically-acceptable acid addition salts of those compounds of the present invention having a free amino group are also readily prepared by standard methods. For example, an equivalent of the acid is combined with amine in an organic or an aqueous solvent. The salt is isolated by concentration and/or the addition of a non-solvent. If desired, the salt can generally be isolated directly from a reaction mixture, without isolation of the free amine. Pharmaceutically-acceptable acid addition salts include, but are not limited to, hydrochloric acid, sulfuric acid, nitric acid, phosphoric acid, citric acid, maleic acid, succinic acid, p-toluenesulfonic acid and methanesulfonic acid.

The utility of bis-ester compounds of the formula (1) is as exceptionally broad spectrum, systemic antibacterial agents. These compounds are useful clinically in the treatment of mammalian infections caused by any one of this broad spectrum of sensitive bacteria. The systemic utility of these compounds results from their in vivo hydrolysis to the mixture of penicillin antibiotic and, the potent beta-lactamase inhibitor, viz., [6-beta-(hydroxymethyl)penicillanic acid 1,1-dioxide] of the formula (6).

The ultimate clinical utility of the bis-ester compounds against particular pathogenic bacteria is reflected by in vitro measurements of the activity of the compound (6) against bacterially derived beta-lactamases, as well as by measuring the minimum inhibitory concentrations of a 1:1 combination of the penicillin with the beta-lactamase inhibitory compound (6). The detailed description and typical results of such studies follows.

The compounds of the present invention are thus evaluated in vitro by the ability of the compound (13) to inhibit the hydrolysis of certain beta-lactam antibiotics by beta-lactamase enzymes. The hydrolysis of ampicillin and penicillin G was determined by the microiodometric method of Novick [Biochem, J. 83, 236 (1962)]. Conditions for this assay are 0.5 M potassium phosphate, pH 6.5 and 37° C. Reactions were initiated by the addition of the cell-free beta-lactamase, except in the case of preincubation experiments in which the inhibitor and enzyme were incubated together in the assay mixture for 10 minutes before initiation of the reaction by addition of substrate. With the cell-free extracts of *Staphylococcus aureus*, *Escherichia coli*, *Klebsiella pneumoniae* and *Pseudomonas aeruginosa*, the substrate was ampicillin at 33 micro M (13 microg./ml). Typical specific activities of the beta-lactamase preparations were, respectively, 6,019, 88,970, 260 and 76 micromol/hr. per mg. of protein. Penicillin G (33 micromol) was the substrate used with the *Enterobacter cloacae* beta-lactamase, which showed a typical specific activity of 10,080 micromol/hr. per mg of protein.

Cell-free extracts were prepared by sonic treatment (using three 30-s bursts at 4° C. except for *S. aureus*, which was broken with a French press) of cultures grown in brain heart infusion on a rotary shaker incubator. For the *S. aureus*, *P. aeruginose*, and *E. cloacae* strains, de novo synthesis of beta-lactamase was induced by growing a log-phase culture in the presence of a sublethal concentration of penicillin G at 100, 1,000, and 300 microg./ml, respectively, for 2.5 hr.

The beta-lactamase inhibiting activities of the compound (6) and of sodium penicillanic acid 1,1-dioxide are summarized in Table I. Especially noteworthy is the activity of compound (A) against beta-lactamase producing strains of *Pseudomonas aeruginosa* and *Enterobacter cloacae* against which the earlier beta-lactamase inhibitor, penicillanic acid 1,1-dioxide, shows at best a low order of activity.

TABLE I

Activity of Compounds As Inhibitors of Cell Free Beta-Lactamases

A. 6-beta-(Hydroxymethyl)penicillanic acid 1,1-dioxide (as calcium salt).
B. Penicillanic acid 1,1-dioxide (as sodium salt)

| Source of Beta-Lactamsase | Antibiotic (conc.) | A/B | Inhibitor (conc.) | % Inhibition Beta-Lactam Hydrolysis |
|---|---|---|---|---|
| *Staphylococcus aureus* 01A400 | Ampicillin (33 μM) | A | 66 μM | 98.3 |
| | | | 16.5 | 78.8 |
| | | | 1.0 | 39.3 |
| | | B | 66 | 100 |
| | | | 16.5 | 95 |
| | | | 1.0 | 0 |
| *Escherichia coli* 51A129 | Ampicillin (33 μM) | A | 66 | 100 |
| | | | 16.5 | 100 |
| | | | 1.0 | 95.7 |
| | | | 0.67 | 92.1 |
| | | B | 66 | 100 |
| | | | 16.5 | 100 |
| | | | 1.0 | 97.0 |
| *Klebsiella pneumoniae* 53A129 | Ampicillin (33 μM) | A | 66 | 100 |
| | | | 16.5 | 100 |
| | | | 1.0 | 81.2 |
| | | B | 66 | 100 |
| | | | 16.5 | 100 |
| *Pseudomonas aeruginosa* 52A104 | Penicillin G (33 μM) | A | 66 μM | 98.8 |
| | | | 16.5 | 93.4 |
| | | | 1.0 | 21.7 |
| | | B | 66 | 0 |
| | Ampicillin (33 μM) | B | 66 | 27.5 |
| | | | 16.5 | 5.0 |
| *Enterobacter cloacae* 67B009 | Penicillin G (33 μM) | A | 66 | 77.0 |
| | | | 16.5 | 52.0 |
| | | | 1.0 | 11.4 |
| | | B | 66 | 0 |
| | | | 16.5 | 0 |
| | | | 1.0 | 0 |
| | | | 66[a] | 26 |

[a]Preincubation (see text)

The in vitro activity of the compounds of the present invention is demonstrated by measuring the minimum inhibitory concentrations (MIC's) in mcg/ml of compound (6) together with the penicillin against a variety of microorganisms. The procedure which is followed is the one recommended by the International Collaborative Study on Antibiotic Sensitivity Testing [Ericcson and Sherris, Acta. Pathologica et Microbiologia Scandinav, Supp. 217, Sections A and B: 64–68 (1971)], and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading tubes after 18 hrs. at 37° C. The susceptibility (MIC) of the test organism is accepted as the lowest concentration of compound capable of producing complete inhibition of growth as judged by the naked eye. The manner in which the said compounds of the formula (B) increase the effectiveness of a beta-lactam antibiotic can be appreciated by reference to experiments in which the MIC of a given antibiotic alone, and a compound of the formula (6) alone, are measured. These MIC's are then compared with the MIC values obtained with a combination of the given antibiotic and the compound of the formula (6). When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

Results of experiments illustrating that the compound of the formula (6) enhances the effectiveness of ampicillin are reported in Table II. For purposes of comparison data on the earlier beta-lactamase inhibitor, penicillanic acid 1,1-dioxide, are included. The enhanced spectrum and potency (synergy or pronounced synergy) of compound (6) will be noted.

TABLE II

MIC Values for 1:1 Mixtures of Ampicillin and beta-Lactamase Inhibitors

C. 6-beta-(Hydroxymethyl)penicillanic acid 1,1-Dioxides (sodium salt)
D. Penicillanic acid 1,1-dioxide (sodium salt)
E. Ampicillin

| Microorganism | MIC Values D | 1:1D:E | Response[a] D | MIC Values C | 1:1C:E | Response[a] C |
|---|---|---|---|---|---|---|
| *Staphylococcus aureus* 01A005 | 100 | ≦0.2 | NT | >200 | 0.39 | AT |
| *Staphylococcus aureus* 01A400 | 200 | 3.12 | PS | >200 | 3.12 | PS |
| *Escherichia coli* 51A266 | 25 | 3.12 | N | 50 | 3.12 | N |
| *Citrobacter diversus* 70C031 | 200 | 12.5 | PS | 200 | 25 | PS |
| *Escherichia coli*-R 51A129 | 200 | 100 | A | 50 | 12.5 | S |
| *Pseudomonas* | | | | | | |

TABLE II-continued

MIC Values for 1:1 Mixtures of Ampicillin and beta-Lactamase Inhibitors

C. 6-beta-(Hydroxymethyl)penicillanic acid 1,1-Dioxides (sodium salt)
D. Penicillanic acid 1,1-dioxide (sodium salt)
E. Ampicillin

| Microorganism | MIC Values D | 1:1 D:E | Response[a] D | MIC Values C | 1:1 C:E | Response[a] C |
|---|---|---|---|---|---|---|
| aeruginosa 52A104 | >200 | >100 | NT | >200 | 100 | S |
| Klebsiella pneumoniae 53A079 | 50 | 12.5 | S | 50 | 6.25 | PS |
| Proteus morgani 57G001 | 200 | 12.5 | PS | >200 | 1.56 | PS |
| Serratia marcescens 63A095 | 200 | 6.25 | PS | 200 | 6.25 | PS |
| Enterobacter cloacae 67B009 | 100 | 25 | S | 100 | 12.5 | PS |

[a]PS = Pronounced Synergy
S = Synergy
A = Additive
N = Nothing
AT = Antagonism
NT = No Test When using an antibacterial compound of this invention in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the preferred oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g., polyethylene glycols having molecular weights of from 2000 to 4000. When aqueous suspensions are required for oral use, the active ingredient is combined with emulsifying and suspending agents. If desired, certain sweetening and/or flavoring agents can be added.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally and parenterally at dosages in the range from about 5 to about 100 mg per kilogram of body weight per day, usually in divided doses. In some instances it may be necessary to use doses outside these ranges.

The present invention is illustrated by the following examples. However, it should be understood that the invention is not limited to the specific details of these examples.

EXAMPLE 1

Chloromethyl 6,6-Dibromopenicillanate 6,6-Dibromopenicillanic acid [Clayton, J. Chem. Soc. C, p. 2123 (1969); 25 g] was combined with 100 ml of methylene chloride and 25 ml of water and the pH adjusted to 8.0 with 40% tetrabutylammonium hydroxide over a period of 15 minutes. The methylene chloride layer was separated and the aqueous layer extracted with three 3.5 ml portions of fresh methylene chloride. The methylene chloride layers were combined, dried over anhydrous sodium sulfate, filtered, and evaporated in vacuo to yield tetrabutylammonium 6,6-dibromopenicillanate (39.0 g) as a viscous oil. The salt was combined with 125 ml of chloroiodomethane and the mixture stirred for 16 hours, concentrated to dryness in vacuo and the residue chromatographed on 1 kg of silica gel with 19:1 toluene: ethyl acetate as eluant and tlc monitoring [Rf 0.75 (1:1 hexane:ethyl acetate)]. Pure product fractions were combined, evaporated to dryness, and the residue recrystallized from ether-petroleum ether to yield the title product in two crops (14.1 g and 1.2 g); pnmr/CDCl$_3$/delta (ppm) 1.6 (s, 3H), 1.75 (s, 3H), 4.62 (s, 1H), 5.8 (dd, 2H), 5.82 (s, 1H); m.p. 105°–106° C.

By the same method, but substituting 1-chloro-1-iodoethane for chloroiodomethane, 1-chloroethyl 6,6-dibromopenicillanate is prepared.

By the same method, but substituting methylene bis-mesylate, methylene bis-tosylate, methylene bis(phenylsulfonate) or methylene bis(n-butylsulfonate) for chloroiodomethane, the following compounds are prepared:
mesyloxymethyl 6,6-dibromopenicillanate;
benzenesulfonyloxymethyl 6,6-dibromopenicillanate; and
tosyloxymethyl 6,6-dibromopenicillanate.

EXAMPLE 2

Chloromethyl 6-alpha-Bromo-6-beta-(hydroxymethyl)penicillanate
and
Chloromethyl 6-beta-Bromo-6-alpha-(hydroxymethyl)penicillanate The title compound of the preceding Example (14.1 g) was combined with 175 ml of dry tetrahydrofuran and cooled to −78° C. tert-Butylmagnesium chloride (12.8 ml of 2.7 M in tetrahydrofuran) was added dropwise over 10 minutes, while maintaining the temperature less than −65° C. The reaction mixture was stirred for an additional 30 minutes at −78° C. Dry paraformaldehyde (45 g) heated at 150° C., under nitrogen, with an oil bath, was fed as formaldehyde by a slow stream of nitrogen into the reaction mixture over a 4 hour period. Acetic acid (5 ml) was added to the cold reaction mixture, which was then warmed to room temperature, concentrated in vacuo, taken up in ethyl acetate, and washed sequentially with 200 ml 1 N hydrochloric acid, 2×100 ml of water and 100 ml of saturated brine, dried over anhydrous sodium sulfate, and concentrated to an oil. The oil was chromatographed on 600 g silica gel using 9:1 toluene:ethyl acetate and then 4:1 toluene:ethyl acetate as eluant and tlc monitoring. Title products were obtained in about 1:5 ratio of beta-hydroxymethyl to alpha-hydroxymethyl as an oil [5.2 g; Rf 0.12, 0.18 (4:1 toluene:ethyl acetate); pnmr/CDCl$_3$/delta (ppm) 1.58 (s, 3H), 1.7 (s, 3H), 2.4–2.85 (m, 1H), 4.13 (broad s, 2H), 4.54 (s, 1H), 5.52 (s, 1H), 5.75 (dd, 2H)].

By the same method the 1-chloroethyl ester of the preceding Example is converted to 1-chloroethyl 6-alpha-bromo-6-beta-(hydroxymethyl)penicillanate and 1-chloroethyl 6-beta-bromo-6-alpha(hydroxymethyl)-penicillanate.

By the same method the sulfonyloxymethyl esters of the preceding Example are converted to the corresponding mesyloxymethyl, benzenesulfonyloxymethyl and tosyloxymethyl esters.

EXAMPLE 3

Chloromethyl 6-beta-(Hydroxymethyl)penicillanate

The mixture of title products of the preceding Example (4.5 g, 12.5 mmoles) combined with benzene (75 ml) and tributyltin hydride (3.48 ml, 13.1 mmoles) and heated to reflux. Tlc monitoring indicated reaction was complete within 2 hours. The reaction mixture was cooled and concentrated in vacuo to a viscous oil which gave a gum on trituration with hexane. The gum was chromatographed on 200 g of silica gel eluting with 1:1 toluene:ethyl acetate and collecting 25 ml fractions. Clean product fractions 19–32 were combined and evaporated to yield the title product as a viscous oil [2.8 g; ir (nujol) 1775 cm$^{-1}$; pnmr/CDCl$_3$/delta(ppm) 1.56 (s, 3H), 1.68 (s, 3H), 2.18–2.42 (m, 1H), 3.78–4.12 (m, 3H), 4.4 (s, 1H), 5.42 (d, 1H), 5.74 (dd, 2H); Rf 0.34 (1:1 toluene:ethyl acetate)].

By the same method, the mixture of 1-chloroethyl esters of the preceding Example is converted to 1-chloroethyl 6-beta-(hydroxymethyl)penicillanate.

By the same method, the sulfonyloxymethyl esters of the preceding Example are converted to the corresponding mesyloxymethyl, benzenesulfonyloxymethyl and tosyloxymethyl esters.

EXAMPLE 4

Chloromethyl 6-beta-(Hydroxymethyl)penicillanate 1,1-Dioxide

The title product of the preceding Example (2.8 g.) was combined with ethyl acetate (50 ml) and cooled to 0° C. m-Chloroperbenzoic acid (2.24 g) was added. After 15 minutes the reaction mixture was checked by tlc; complete conversion to the 1-oxide [Rf 0.09 (1:1 toluene:ethyl acetate)] was indicated. Additional m-chloroperbenzoic acid (2.24 g) was added and the mixture stirred for 16 hours at room temperature, by which time tlc indicated complete conversion to the dioxide. Water (50 ml) was added to the reaction mixture and any excess peroxides destroyed with sodium bisulfite. The pH was adjusted to 7.5 and the organic layer separated, washed sequentially with 25 ml portions of saturated sodium bicarbonate, water and brine, dried over anhydrous sodium sulfate, filtered, and concentrated to yield the title product as a gum [2.6 g; ir (nujol) 1780 cm$^{-1}$ pnmr/CDCl$_3$/delta(ppm) 1.48 (s, 3H), 1.62 (s, 3H), 2.8–3.15 (broad s, 1H), 4.2 (broad s, 2H), 4.08–4.5 (m, 1H), 4.5 (s, 1H), 4.68–4.83 (m, 1H), 5.8 (dd, 2H)].

By the same method the 1-chloroethyl ester of the preceding Example is converted to 1-chloroethyl 6-beta-(hydroxymethyl)penicillanate 1,1-dioxide.

By the same method the sulfonyloxymethyl esters of the preceding Example are converted to the corresponding mesyloxymethyl, benzenesulfonyloxymethyl and tosyloxymethyl esters.

EXAMPLE 5

Iodomethyl 6-beta-(Hydroxymethyl)penicillanate 1,1-Dioxide

Title product of the preceding Example (2.4 g) was combined with 30 ml of acetone and sodium iodide (5.77 g) and the mixture stirred for 16 hours. The reaction mixture was concentrated in vacuo to oily solids, which were distributed between 75 ml of ethyl acetate and 50 ml of water. The ethyl acetate was separated, washed in sequence with two 25 ml portions of water and one 25 ml portion of brine, dried over anhydrous sodium sulfate, filtered and concentrated in vacuo. The residue was chromatographed on 200 g of silica gel, eluting with 7:3 ethyl acetate:methylene chloride and collecting 20 ml fractions. Clean product-containing fractions 14–25 were combined and evaporated to yield title product as a tacky foam [2.4 g; ir (nujol) 1780 cm$^{-1}$; Rf 0.64 (7:3 ethyl acetate:methylene chloride); pnmr/CDCl$_3$/delta(ppm) 1.48 (s, 3H), 1.6 (s, 3H), 2.8–3.15 (broad s, 1H), 4.2 (broad s, 2H), 4.1–4.42 (m, 1H), 4.68–4.8 (m, 1H), 5.94 (dd, 2H)].

By the same method, extending the reaction time to 24 hours, the 1-chloroethyl ester of the preceding Example is converted to 1-iodoethyl 6-beta-(hydroxymethyl)penicillanate 1,1-dioxide.

By the same method, substituting sodium bromide for sodium iodide and extending the reaction time to 32 hours, bromomethyl 6-beta-(hydroxymethyl)penicillanate 1,1-dioxide is prepared.

The title product is also prepared by reacting the corresponding mesyloxymethyl, benzenesulfonyloxymethyl and tosylsulfonyloxymethyl esters with sodium iodide, but again extending the reaction time to 24 hours.

EXAMPLE 6

6-beta-(D-2-Azido-2-phenylacetamido)penicillanoyloxymethyl 6'-beta-(Hydroxymethyl)penicillanate 1',1'-Dioxide A mixture of 3.5 g of 6-(D-2-alpha-azidophenylacetamido)penicillanic acid sodium salt in 20 ml of methylene chloride and 20 ml of water was treated with sufficient 6 N hydrochloric acid to give a pH of 2.0. Tetrabutylammonium hydroxide (40% in water) was gradually added until the pH was 7.0. The organic phase was separated and the aqueous layer further extracted (2×20 ml) with fresh methylene chloride. The methylene chloride layers were combined, dried over sodium sulfate and concentrated under vacuum to give 4.2 g of the corresponding tetrabutylammonium salt.

The tetrabutylammonium salt (1.65 g, 2.7 mmmoles) and the iodomethyl ester of the preceding Example (1.07 g, 2.7 mmoles) were combined in 20 ml of acetone and stirred to dissolve. Tlc monitoring (1:1 ethyl acetate:toluene) indicated that the reaction was almost complete within 3 minutes of dissolution. After an additional 10 minutes, the reaction mixture was evaporated in vacuo to a foam which was chromatographed on silica gel with 3:2 methylene chloride:ethyl acetate as eluant, collecting 20 ml fractions. Clean product fractions (tlc) were combined and concentrated in vacuo to yield title product as a foam [1.7 g; Rf 0.12 (1:1 ethyl acetate:toluene), 0.43 (3:2 methylene chloride:ethyl acetate), 0.5 (1:1 methylene chloride:ethyl acetate); pnmr/CDCl$_3$/delta(ppm) 1.4, 1.5, 1.54, 1.61 (4s, 4×3H), 2.3–2.6 (m, 1H), 4.0–4.5 (m, 3H), 4.4 (s, 2H), 5.0 (s, 1H), 5.4–5.8 (m, 2H), 5.8 (broad s, 2H), 7.05 (d, 1H), 7.3 (s, 5H)].

By the same method, the 1-iodoethyl ester of the preceding Example is converted to 1-[6-beta-(D-2-azido-2-phenylacetamido)penicillanoyloxy]ethyl 6'-beta-(hydroxymethyl)penicillanate 1',1'-dioxide.

Substituting an equivalent amount of the appropriate tetrabutylammonium salt (prepared by the same method from the corresponding penicillin), the following compounds are prepared from iodomethyl 6-beta-(hydroxymethyl)penicillanate 1,1-dioxide:

6-beta-(2-phenylacetamido)penicillanoyloxymethyl 6'-beta-(hydroxymethyl)penicillanate 1',1'-dioxide;
6-beta-(2-phenoxyacetamido)penicillanoyloxymethyl 6'-beta-(hydroxymethyl)penicillanate 1',1'-dioxide;
6-beta-(2-benzyloxycarbonyl-2-phenylacetamido)-penicillanoyloxymethyl 6'-beta-(hydroxymethyl)-penicillanate 1',1'-dioxide;
6-beta-[2-benzyloxycarbonyl-2-(2-thienyl)acetamido]-penicillanoyloxymethyl 6'-beta-(hydroxymethyl)-penicillanate 1',1'-dioxide;
6-beta-[2-benzyloxycarbonyl-2-(3-thienyl)acetamido]-penicillanoyloxymethyl 6'-beta-(hydroxymethyl)-penicillanate 1',1'-dioxide; and
6-beta-[2-(4-ethyl-2,3-dioxopiperazine-1-carboxamido)-2-phenylacetamido]penicillanoyloxymethyl 6'-beta-(hydroxymethyl)penicillanate 1',1'-dioxide.

The title product is also prepared by reacting the corresponding chloromethyl, bromomethyl, mesyloxymethyl, benzenesulfonyloxymethyl and tosyloxymethyl esters of the preceding two Examples, monitoring the reaction by tlc and extending the reaction time as necessary. When the latter esters are employed, it is preferable to add iodide ion to enhance the overall rate of conversion to the desired product.

EXAMPLE 7

6-beta-(D-2-Amino-2-phenylacetamido)penicillanoyloxymethyl 6'-beta-(Hydroxymethyl)penicillanate 1',1'-Dioxide Title compound of the preceding Example (1.4 g) was combined with 30 ml of methylene chloride and 30 ml of isopropyl alcohol and hydrogenated at 50 psi for 45 minutes over 1.5 g of 10% Pd/C. Tlc control indicated reaction to be about 75% complete. An additional portion (1.5 g) of catalyst was added and hydrogenation continued for 45 minutes. Since a trace of starting material remained, more catalyst (1 g) was added and hydrogenation allowed to proceed for a further 30 minutes. The catalyst was recovered by filtration with 1:1 methylene chloride:isopropyl alcohol wash. The combined filtrate and washes were evaporated to solids. The residue was triturated with ether and filtered to yield the title product [0.83 g; ir (nujol) 1735–1800 cm$^{-1}$; pnmr/DMSO-d$_6$/delta(ppm) 1.38, 1.39, 1.42 and 1.5 (4s, 12H), 3.6–4.35 (m, 3H), 4.42 (s, 1H), 4.55 (s, 1H), 4.81 (s, 1H), 5.1–5.26 (m, 1H), 5.38–5.62 (m, 2H), 5.9 (broad s, 2H), 7.4 (broad s, 5H)].

By the same method the corresponding 1,1-ethanediol bis-ester from the preceding Example is converted to 1-[6-beta-(D-2-amino-2-phenylacetamido)-penicillanoyloxy]ethyl 6'-beta-(hydroxymethyl)penicillanate 1',1'-dioxide.

By the same method the benzyl esters of the preceding Example are hydrogenolyzed to yield:

6-beta-(2-carboxy-2-phenylacetamido)penicillanoyloxymethyl 6'-beta-(hydroxymethyl)penicillanate 1',1'-dioxide;
6-beta-[2-carboxy-2-(2-thienyl)acetamido]penicillanoyloxymethyl 6'-beta-(hydroxymethyl)penicillanate 1',1'-dioxide; and
6-beta-[2-carboxy-2-(3-thienyl)acetamido]pencillanoyloxymethyl 6'-beta-(hydroxymethyl)pencillanate 1',1'-dioxide.

EXAMPLE 8

6-beta-(D-2-Amino-2-phenylacetamido)penicillanoyloxymethyl 6'-beta-(Hydroxymethyl)penicillanate 1',1'-Dioxide Hydrochloride Hydrochloric acid (0.1 N, 12.5 ml) was cooled to 0° C. and 0.78 g of the corresponding free base from the preceding Example added. The mixture was stirred for 5 minutes to yield a hazy solution having pH 1.9. The solution was clarified by filtration over a pad of diatomaceous earth with 30 ml water wash. The filtrate and wash were combined and freeze dried to yield the title product [0.76 g; ir (nujol) 1730–1800 cm$^{-1}$; pnmr/DMSO-d$_6$/delta(ppm) 1.2–1.62 (m, 12H), 3.5–4.3 (m, 3H), 4.38 (s, 1H), 4.5 (s, 1H), 4.8–5.7 (m, 4H), 5.88 (broad s, 2H), 6.75 (d, 2H), 7.22 (d, 2H), 8.5–9.1 (broad s, 2H), 9.4 (d, 1H), 9.8–10.2 (broad s, 1H)].

EXAMPLE 9

6-beta-[D-2-Benzyloxycarbonylamino-2-(p-hydroxyphenyl)acetamido]penicillanoyloxymethyl 6'-beta-(Hydroxymethyl)penicillanate 1',1'-Dioxide 6-beta-[D-2-Benzoyloxycarbonylamino-2-(p-hydroxyphenyl)acetamido]penicillanic acid ("carbobenzoxy amoxicillin", 5.0 g) was combined with 75 ml of methylene chloride and 25 ml of water. Gumming of the solids was noted. The pH was adjusted to 8.5 with 40% tetrabutylammonium hydroxide; the gummy solids dissolving. The methylene chloride layer was separated and the aqueous layer extracted with two further 40 ml portions of methylene chloride. The methylene chloride organic layer and extracts were combined and evaporated to yield the corresponding tetrabutylammonium salt (7.2 g).

Tetrabutylammonium salt prepared in this manner (3.33 g, 4.5 mmoles) was combined with iodomethyl 6-beta-(hydroxymethyl)penicillanate 1,1-dioxide (1.25 g, 3.1 mmoles) in 15 ml of acetone. The reaction was monitored by tlc, which indicated almost complete reaction after 5 minutes and no more than a trace of starting material after 30 minutes. The reaction mixture was concentrated in vacuo to a viscous gum. The residue was taken up in 15 ml of 7:3 ethyl acetate:methylene chloride and chromatographed on 125 g of silica gel using the same solvent system as eluant and tlc monitoring. Product-containing fractions were combined and evaporated to yield 1.8 g of partially purified product. The latter was rechromatographed to yield purified title product [1.25 g; Rf 0.32 (7:3 ethyl acetate:methylene chloride); pnmr/DMSO-$d_6$/delta(ppm) 1.4, 1.42, 1.48, 1.58 (4s, 12H), 3.55–4.3 (m, 3H), 4.4 (s, 1H), 4.59 (s, 1H), 5.06 (s, 2H), 5.05–5.3 (m, 2H), 5.32–5.68 (m, 2H), 5.95 (broad s, 2H), 6.68 (d, 2H), 7.2 (d, 2H), 7.34 (s, 5H), 7.78 (d, 1H), 8.9 (d, 1H), 9.4 (s, 1H)].

In like manner, tetrabutylammonium salt is reacted with 1-iodoethyl 6-beta-(hydroxymethyl)penicillanate 1,1-dioxide to produce the corresponding bis 1,1-ethanediol ester.

In like manner, 6-beta-(benzyloxycarbonylamino)-penicillanic acid is converted to its tetrabutylammonium salt and then reacted with iodomethyl 6-beta-(hydroxymethyl)penicillanate 1,1-dioxide to yield 6-beta-(benzyloxycarbonylamino)penicillanoyloxymethyl 6'-beta-(hydroxymethyl)penicillanate 1',1'-dioxide.

EXAMPLE 10

6-beta-[D-2-Amino-2-(p-hydroxyphenyl)acetamido]-penicillanoyloxymethyl 6'-beta-(Hydroxymethyl)penicillanate 1',1'-Dioxide The title ester of the preceding Example (1.2 g) was combined with 15 ml of isopropyl alcohol and 15 ml of methylene chloride and hydrogenated at 50 psi over 1.5 g of 10% Pd/C for 45 minutes, at which time tlc monitoring indicated the reaction was about 50% complete. An additional 1.5 g of catalyst was added and hydrogenation continued for a further 45 minutes to about 80% completion by tlc. A third 1.5 g portion of catalyst and 45 minutes hydrogenation left no more than a trace of starting material. The catalyst was recovered by filtration. Evaporation of the filtrate in vacuo to solids and trituration with ether gave the title product [0.42 g; pnmr/DMSO-$d_6$/delta(ppm) 1.38, 1.42, 1.5 (s, 12H), 3.5–4.25 (m, 3H), 4.38 (s, 1H), 4.52 (s, 1H), 4.8–5.7 (m, 4H), 5.88 (broad s, 2H), 6.72 (d, 2H), 7.22 (d, 2H)].

In like manner, the bis 1,1-ethanediol ester of the preceding Example is hydrogenolyzed to the corresponding bis ester of 1,1-ethanediol with amoxicillin and 6-beta-(hydroxymethyl)penicillanate 1,1-dioxide.

In like manner, the 6-benzyloxycarbonylamino derivative of the preceding Example is hydrogenolyzed to yield 6-beta-aminopenicillanoyloxymethyl 6'-beta-(hydroxymethyl)penicillanate 1,1-dioxide.

EXAMPLE 11

6-beta-[D-2-Amino-2-(p-hydroxyphenyl)acetamido]-penicillanoyloxymethyl 6'-beta-(Hydroxymethyl)penicillanate 1',1'-Dioxide Hydrochloride By the procedure of Example 8, title product of the preceding Example (0.38 g) was converted to the title hydrochloride salt [0.33 g; pnmr/DMSO-$d_6$/delta(ppm) 1.2–1.62 (m, 12H), 3.5–4.3 (m, 3H), 4.38 (s, 1H), 4.5 (s, 1H), 4.8–5.7 (m, 4H), 5.88 (broad s, 2H), 6.75 (d, 2H), 7.22 (d, 2H), 8.5–9.1 (broad s, 2H), 9.4 (d, 1H), 9.8–10.2 (broad s, 1H)].

EXAMPLE 12

6-beta-(2-Phenylacetamido)penicillanoyloxymethyl 6'-beta-(Hydroxymethyl)penicillanate 1',1'-Dioxide 6-beta-Aminopenicillanoyloxymethyl 6'-beta-(hydroxymethyl)penicillanate 1',1'-dioxide of the preceding Example and a molar equivalent of triethylamine are taken into 25 parts by weight of methylene chloride. A molar equivalent of 2-phenylacetyl chloride in 5 parts by weight of methylene chloride is added dropwise while maintaining the temperature of the reaction mixture at 20°–25° C. After 2 hours at the same temperature, by-product triethylamine hydrochloride is extracted into water. The methylene chloride layer is dried over anhydrous sodium sulfate, filtered and evaporated to yield the title product.

EXAMPLE 13

6-beta-(2,2-Dimethyl-4-phenyl-5-imidazolidinon-1-yl)penicillanoyloxymethyl 6'-beta-(Hydroxymethyl)penicillanate 1',1'-Dioxide 6-beta-(2-Amino-2-phenylacetamido)penicillanoyloxymethyl 6'-beta-(hydroxymethyl)penicillanate 1',1'-dioxide (0.5 g) is stirred with 30 ml of acetone for 3 days. The reaction mixture is evaporated in vacuo to yield the title product.

EXAMPLE 14

Capsules

Capsules are prepared by blending the following ingredients in the proportion by weight indicated:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |
| 6-beta-(D-2-Amino-2-phenylacetamido)-penicillanoyloxymethyl 6'-beta-(hydroxymethyl)penicillanate 1',1'-dioxide hydrochloride | 50.0 |

Appropriate weights of this blend are filled into gelatin capsules of the appropriate size so as to obtain capsules of the following potency of the free base form of the active ingredient: 125 mg, 250 mg and 500 mg.

I claim:
1. A compound of the formula

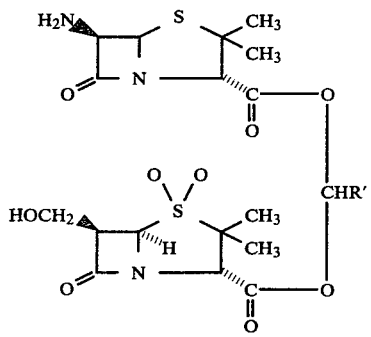

wherein R' is hydrogen or methyl.
2. A compound of claim 1 wherein R' is hydrogen.

3. A compound of the formula

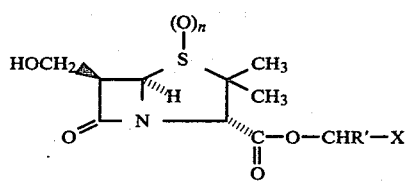

wherein n is zero or an integer of value 1 or 2; R' is hydrogen or methyl; and X is chloro, bromo, iodo, (C$_1$-C$_4$)alkylsulfonyloxy, benzenesulfonyloxy or toluenesulfonyloxy.

4. A compound of claim 3 wherein R' is hydrogen.

5. The compound of claim 4 wherein n is zero and X is chloro.

6. The compound of claim 4 wherein n is 1 and X is chloro.

7. The compound of claim 4 wherein n is 2 and X is chloro.

8. The compound of claim 4 wherein n is 2 and X is iodo.

9. A compound of the formula

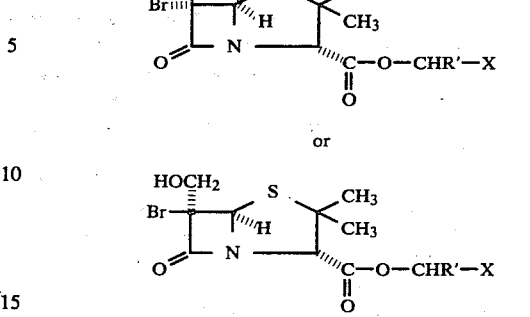

wherein R' is hydrogen or methyl and X is chloro, bromo, iodo, (C$_1$-C$_4$)alkylsulfonyloxy, benzenesulfonyloxy or toluenesulfonyloxy.

10. The compound of claim 9 of the formula

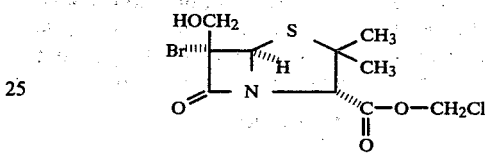

* * * * *